United States Patent
Masini

[19]

[11] Patent Number: 5,897,559

[45] Date of Patent: Apr. 27, 1999

[54] BONE CUTTING GUIDES FOR USE IN THE IMPLANTATION OF PROSTHETIC JOINT COMPONENTS

[75] Inventor: Michael A. Masini, Ann Arbor, Mich.

[73] Assignee: MedIdea, LLC, Ann Arbor, Mich.

[21] Appl. No.: 08/937,216

[22] Filed: Sep. 18, 1997

Related U.S. Application Data

[63] Continuation-in-part of application No. 08/556,812, Nov. 2, 1995, Pat. No. 5,716,361.

[51] Int. Cl.⁶ .................................................. A61B 17/15
[52] U.S. Cl. .............................................. 606/86; 606/82
[58] Field of Search ...................... 606/86, 82, 87, 606/88; 623/20

[56] References Cited

U.S. PATENT DOCUMENTS

| | | | |
|---|---|---|---|
| 3,868,730 | 3/1975 | Kaufer et al. ................................. | 3/1 |
| 4,936,847 | 6/1990 | Manginelli ................................. | 623/23 |
| 4,938,769 | 7/1990 | Shaw ........................................ | 623/20 |
| 4,944,757 | 7/1990 | Martinez et al. ........................... | 623/20 |
| 4,944,760 | 7/1990 | Kenna ....................................... | 623/20 |
| 5,092,869 | 3/1992 | Waldron .................................... | 606/82 |
| 5,122,144 | 6/1992 | Bert et al. ................................. | 606/88 |
| 5,129,909 | 7/1992 | Sutherland ................................. | 606/88 |
| 5,226,915 | 7/1993 | Bertin ....................................... | 623/20 |
| 5,234,433 | 8/1993 | Bert et al. ................................. | 606/88 |
| 5,236,432 | 8/1993 | Masten, III et al. ....................... | 606/88 |
| 5,250,050 | 10/1993 | Poggie et al. ............................. | 606/79 |
| 5,258,032 | 11/1993 | Bertin ....................................... | 606/88 |
| 5,342,367 | 8/1994 | Ferrante et al. ........................... | 606/86 |
| 5,364,401 | 11/1994 | Ferrante et al. ........................... | 606/84 |
| 5,364,402 | 11/1994 | Mumme et al. ........................... | 606/88 |
| 5,458,645 | 10/1995 | Bertin ....................................... | 623/20 |
| 5,464,406 | 11/1995 | Ritter et al. ............................... | 606/86 |
| 5,474,559 | 12/1995 | Bertin et al. .............................. | 606/86 |
| 5,569,259 | 10/1996 | Ferrante et al. ........................... | 606/86 |
| 5,662,656 | 9/1997 | White ....................................... | 606/86 |
| 5,683,397 | 11/1997 | Vendrely et al. .......................... | 606/88 |
| 5,709,689 | 1/1998 | Ferrante et al. ........................... | 606/86 |

Primary Examiner—Michael Buiz
Assistant Examiner—Daphna Shai
Attorney, Agent, or Firm—Gifford, Krass, Groh, Sprinkle, Anderson & Citkowski, PC

[57] ABSTRACT

Improved bone-cutting guides enable a surgeon to better gauge required resection characteristics. A body having an outer surface and an inner surface configured to be positioned against a bone surface to be modified includes one or more openings enabling a bone-cutting tool to be used though the body so as to perform resections beneath the inner surface. To stabilize the bone-cutting tool during the execution of a particular resection, the invention preferably further includes one of more guides which may be temporarily positioned relative to the upper surface of the body. In one embodiment, the outer surface of the body may be shaped to co-act in a joint as part of a trial reduction. For example, the outer surface may be shaped according to a natural proximal tibia, enabling a knee joint reduction to be performed prior to resection. Rather than shaping the outer surface of the body to co-act in a joint as part of a trial reduction, the outer surface of the body may instead be configured to receive an insert featuring the joint-related surfaces.

13 Claims, 4 Drawing Sheets

BONE CUTTING GUIDES FOR USE IN THE IMPLANTATION OF PROSTHETIC JOINT COMPONENTS

REFERENCE TO RELATED APPLICATION

This is a continuation-in-part of U.S. patent application Ser. No. 08/556,812, filed Nov. 2, 1995 now U.S. Pat. No. 5,716,361.

FIELD OF THE INVENTION

This invention concerns arthroplasty, and, more particularly, resides in improved cutting guides having features to better assist a surgeon in preparing a bone, for example, to receive an implant.

BACKGROUND OF THE INVENTION

Whether for primary or revision arthroplasty, cutting guides are typically employed to ensure that any required resections correspond to mating surfaces of the prosthetic component. In knee replacement surgery, for example, a rod is typically inserted into the medullary canal of the proximal tibia, and a cutting guide is temporarily secured to this rod. Such guides include one or more slots into which the blade of an oscillating saw is inserted from anterior to posterior to shape the end of the bone in accordance with corresponding surfaces of the prosthetic element.

Extramedullary guide systems are also familiar to the art and typically provide a means for alignment and securing a cutting block on the proximal tibia.

In the case of a revision, the procedure is usually more elaborate due to deterioration of the previously prepared surfaces resulting from decomposition of the bone/prosthesis interface, necrosis, osteolysis, and other factors. Cutting blocks used in revision procedures therefore include slots corresponding to augments used to fill gaps between major resections and the mating surfaces of the prosthetic component. In the case of proximal tibial repair, such augments are typically wedge-shaped to account for proximal loss. Although more recently introduced techniques attempt to base the cuts on an intramedullary guide to which additional cutting blocks are mounted, there remains an unacceptable margin of error, the correction of which in some cases requires a freehand shaping of the bone. In addition, lateral defects require reshaping without injury to the patellar tendon which obstructs a saw blade when approached from the front of the knee.

SUMMARY OF THE INVENTION

The present invention accordingly provides improved cutting guides which enable one performing a resection to better predict and execute required cut characteristics. Broadly, and in general terms, the invention comprises a body having an outer surface and an inner surface configured to be positioned against a bone surface to be modified. Preferably, the inner surface is substantially flat to mate with a previously executed planar resection. The body further includes one or more openings extending therethrough, from the outer to the inner surface, enabling a bone-cutting tool to be used though the body so as to perform resections below the inner surface. To stabilize the bone-cutting tool during the execution of a particular resection, the invention preferably further includes one or more guides which may be temporarily positioned relative to the upper surface with which the cutting tool physically interacts to perform an accurate cut.

One application of the invention is therefore in proximal tibial preparation as part of a partial or total knee replacement, whether as part of a primary or revision procedure. In this embodiment, the body may be plate-shaped, and affixed to the proximal tibia using an intramedullary stem, or screws, pins or other fastening mechanism appropriate under the circumstances. The openings through the plate may include one or more slots to receive a bone-cutting saw or, alternatively, may take the form of apertures having side surfaces against which a bone-cutting tool or saw may be positioned during resection. The guides in this case are provided in the form of blocks, each having a first surface adapted for positioning against the outer surface of the body, and a second surface used to stabilize the movement of the cutting tool.

In a preferred implementation of the embodiment of the invention used for proximal tibial resection, the body may take the form of a tray of the type used as a sizing plate or final implant, which includes an outer, peripheral lip configured to receive an articular surface insert, which is typically constructed of polyethylene. In this case, the invention may include an insert with a shape corresponding to the final insert, and may be constructed of metal, polymeric or other suitable material, but with slots or other openings which function as cutting guides. As such, the invention may also be used for trialing purposes by reducing the tray and insert with guides into a joint situation and, upon a successful trial reduction, once again exposed and subsequently used as a cutting guide, with confidence that the final implant will fit properly, including any required augments.

DETAILED DESCRIPTION OF THE INVENTION

Figure 1:
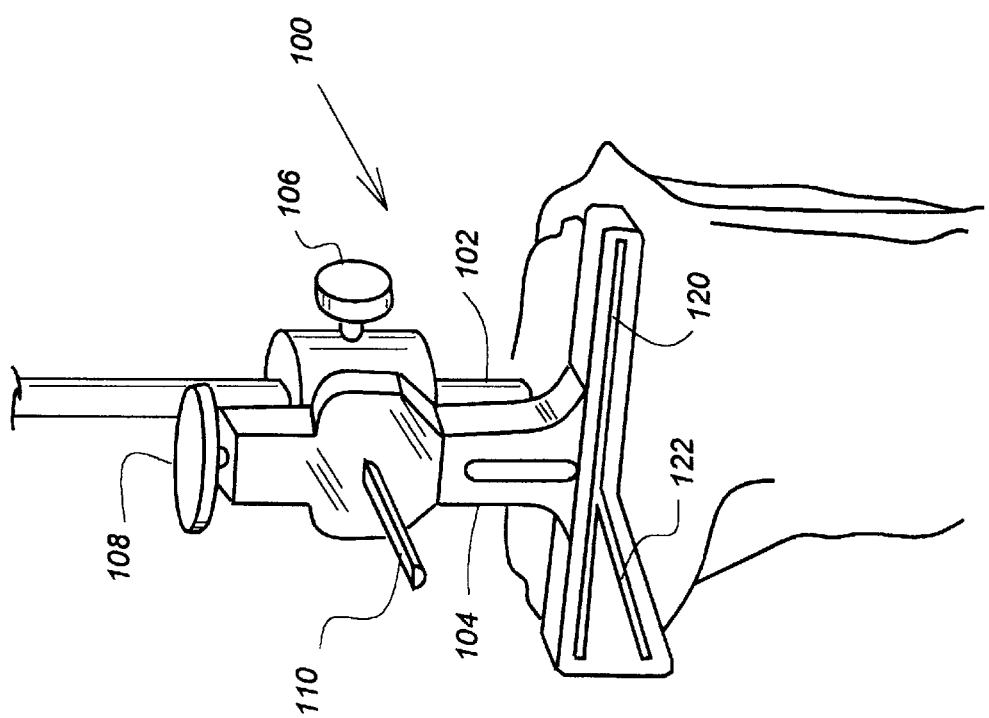
FIG. 1 is an oblique drawing of prior-art apparatus used in conjunction with proximal tibial resection.

FIG. 1 depicts, generally at 100, a prior-art apparatus used in the resection of a proximal tibia in conjunction with knee-replacement surgery. Following the boring of the intramedullary canal, a rod 102 is inserted therein, onto which there is placed an outrigger assembly including slots 120 and 122 to receive a bone-cutting tool such as an oscillating saw (not shown). The up and down positioning of the outrigger may be controlled along rod 102 using knob 106 which is loosened and then tightened at a depth generally below the crown of useful bone, whereas the anterior-posterior positioning may be adjusted along rod 110 using knob 108. Upon achieving a desired orientation and tightening the knobs 106 and 108, the saw is inserted into slot 120 to perform a primary planar resection of the end of the bone, with slot 122 being used to remove wedge-shaped deficiencies, which are typical, and which are ordinarily medial or lateral.

One drawback of this apparatus is that the selection of a particular cutting guide is based upon the type of augmentation required, leading to the need for a wide range of expensive components. According to one such system, if an augmented prosthesis is desired, cutting guides may be selected in accordance with 16° or 26° half wedges, 22° third wedges, 7° full wedges, or 1 or 5 mm blocks.

Figure 2:
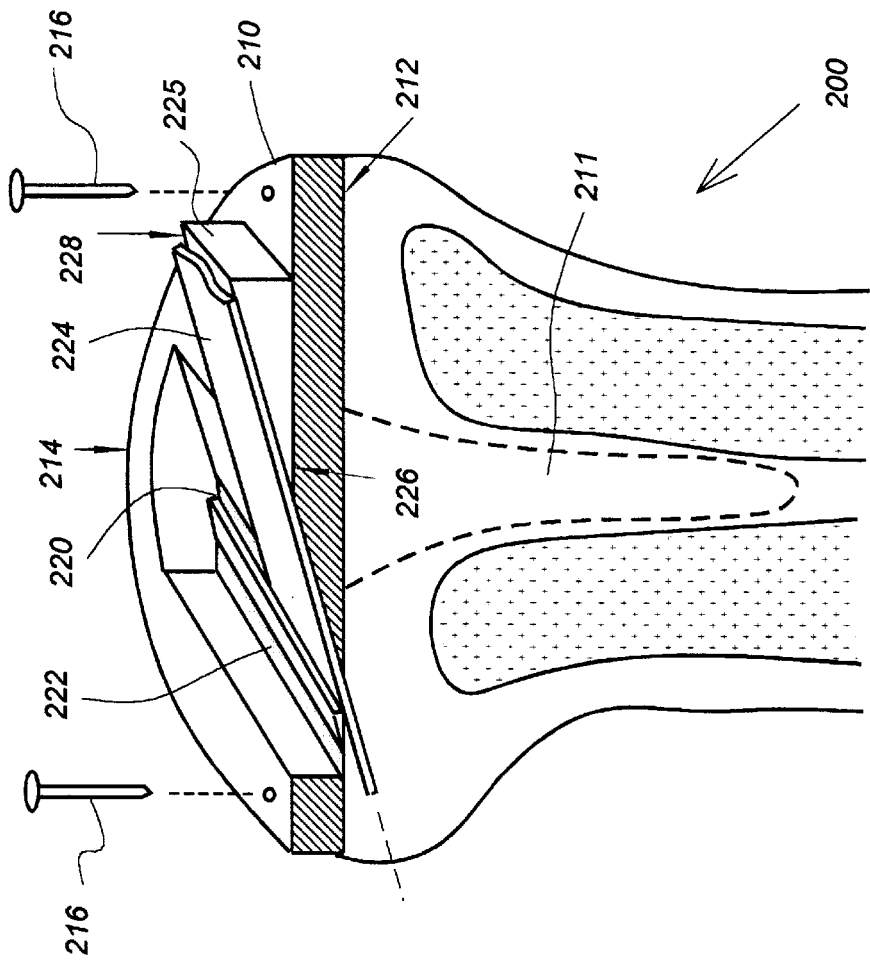
FIG. 2 is a drawing of a cutting guide according to the invention, shown in partial cross-section.

FIG. 2 illustrates one embodiment of the invention adapted for use in modifying the proximal tibia as part of knee-replacement surgery. It will be appreciated, however, that the apparatus of methods of use disclosed with respect to this figure may be readily adapted to other orthopedic situations. Although preferably configured for use in conjunction with a final implant utilizing wedges or augments in predetermined places, the invention is not limited to final implants which utilize augments of a predetermined size, shape or position. Rather, assuming the provision of sufficient slots or guide surfaces as described below, the invention may be used for the resections of a more arbitrary nature.

Continuing the reference to FIG. 2, the invention provides a body 210 having an upper surface 214 and a lower surface 212, the lower surface 212 being adapted to temporarily seat against a surface at the end of the bone, typically formed through a planar resection thereof. The body 210 may be temporarily affixed to the bone using screws or pins 216, or, alternatively, the body may feature a stem 218 to assist in positioning body at a desired orientation.

The body 210 is provided with one or more cutting guides such as slots 220 and 222 into which the blade of a cutting tool such as oscillating saw 224 may be inserted. The invention is not limited to the use of saws for resection, but may readily accommodate osteotomes or other cutting tools such as routers with appropriate modification.

Adjacent the slot(s), a user positions one or more guides such as wedge 225 which include a bottom surface 226 adapted for positioning against the upper surface 214 of the body 210 and a second surface or other feature used as a cutting-tool guide. In this case a second surface 228 of the block 225 is used to stabilize the side of a bone-saw blade, thereby ensuring movement of the tool at a desired angle. To assist in the positioning of a particular guide block, an appropriately shaped recess may be provided with respect to the upper surface 214 of the body 210 to receive the block, as shown.

Figure 3:
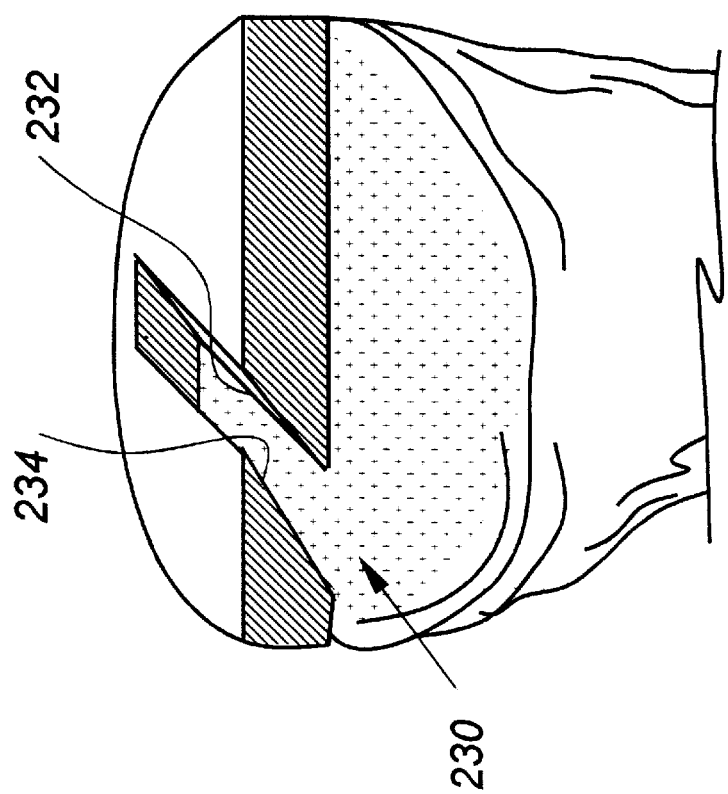
FIG. 3 is a drawing of an alternative cutting guide according to the invention, shown in partial cross-section.

FIG. 3 illustrates an alternative embodiment of the invention wherein, instead of separate slots, the body includes a wider aperture 230 having side surfaces 232 and 234, against which a saw blade may ride to perform either or both of two spaced-apart parallel resections, or non-parallel or variable-angle resections, as appropriate.

Figure 4:
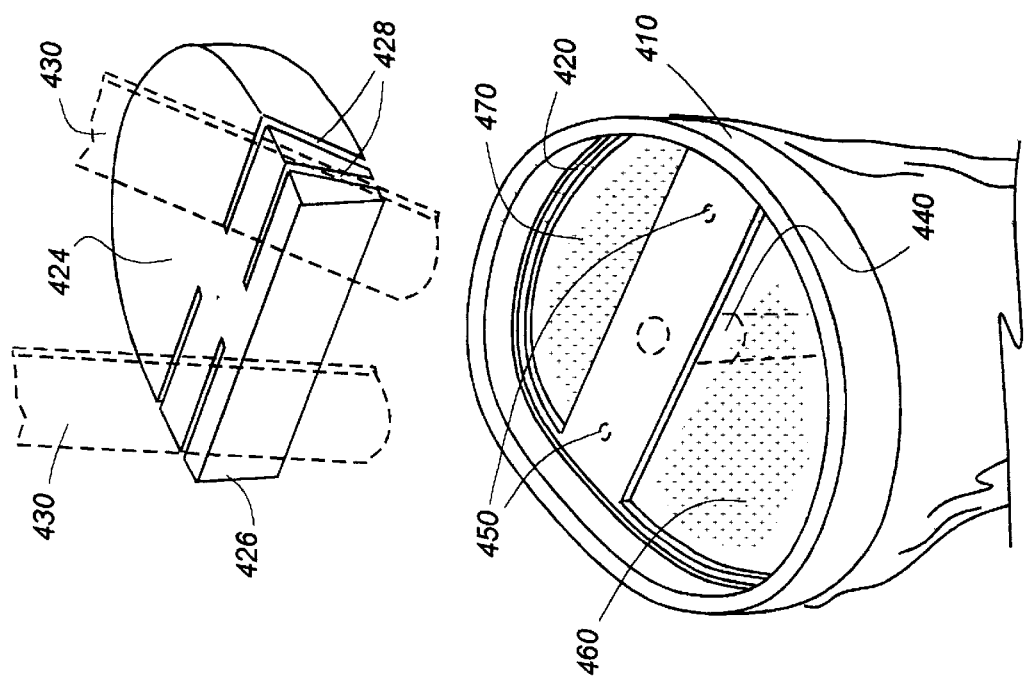
FIG. 4 is an oblique drawing of an alternative embodiment of the invention wherein cutting guides are provided with respect to an insert.

Now turning to FIG. 4, there is shown a different embodiment of the invention wherein the body fastened to the end of the bone assumes the shape of a tray having a lip 420 adapted to receive an insert 424 having one or more surfaces such as 426 or slots 428 used to guide a cutting tool such as oscillating saw 430. The tray-like body 410 may be fastened to the end of the bone through any suitable means, such as an intramedullary rod 440 or pins 450 and includes openings 460 and 470 on either side to permit passage of the cutting tool therethrough without obstruction.

Figure 5:
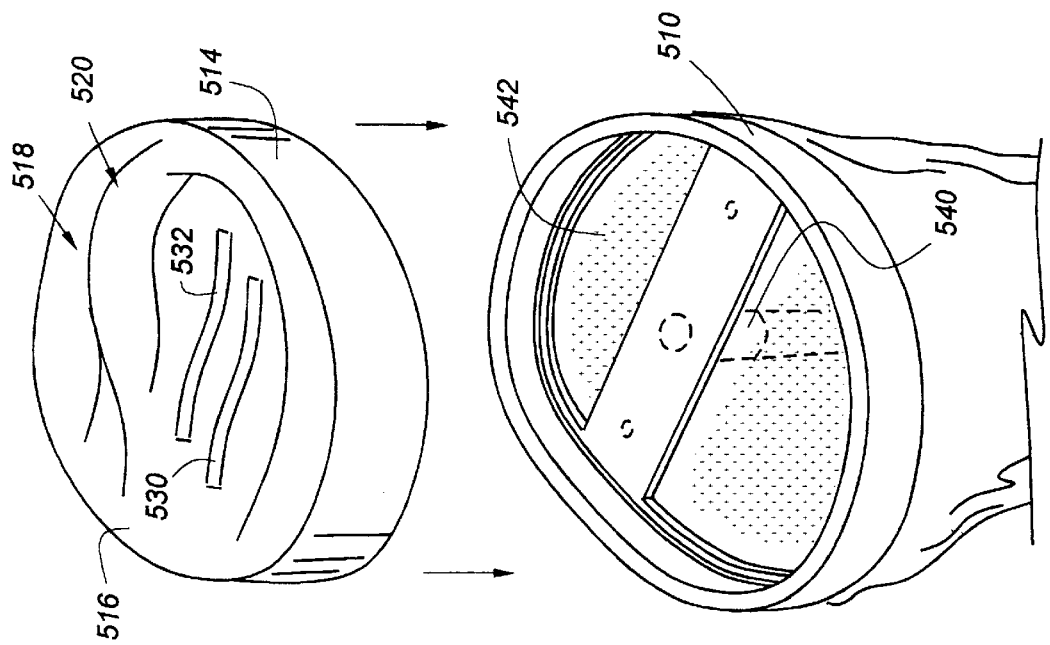
FIG. 5 is an oblique drawing of a further alternative embodiment of the invention wherein the insert includes an articular surface, thereby facilitating a trial reduction prior to resection.

As in the parent to this application, other embodiments of the present invention enable a trial reduction to be performed prior to the execution of further bone resections. Such a configuration is illustrated in FIG. 5, wherein the body positioned against the bone now takes the form of a tray 510 similar or identical to that shown in FIG. 4, which in this case receives an insert associated with joint interactions such as articular surface insert 514 associated with proximal tibial resection. The insert 514 is of the size and shape of that used in a final implant according to existing procedures; that is, it includes depressions 516 and 518 shaped to receive the condyles of the distal femur, and an intercondylar protrusion 520. But in addition, however, one or more slots such as 530 and 532 are provided through the insert 514, and corresponding apertures 540 and 542 are provided in tray 510, such that with the insert 514 positioned within the tray, a trial reduction may be performed, after which the slot(s) may be used as cutting guides. Alternatively, a non-slotted or even final articular insert may be used for trialing purposes, then, assuming an acceptable reduction, this insert could be removed and replaced with one such as that shown in FIG. 5, enabling the cuts to be made after the trial reduction. Although FIG. 5 shows slots 530 and 532, it should be understood that apertures with guide surfaces may alternatively be utilized, and although the figure shows a separate tray-shaped body in insert 514, the body and outer, articular surface may be provided in unitary form while still providing slots or apertures useful as cutting guides subsequent to a trial reduction.

In use, then, the invention affords a procedure which, in at least one respect, is essentially opposite to steps now being performed. That is, rather than making the various cuts (including the use of different saw guides), then performing a trial reduction, by using the present invention, in essence, a trial reduction is performed first with a trial having saw guide slots or surfaces. Once the various cuts have been made, the inventive combined trial/saw guide is removed, at which point the surgeon realizes precisely which final implant to choose for permanent affixation. Not only will the surgeon know which final prosthetic component to select, but he or she will also know which spacers to use based upon the depth of slot used for the cut, and, since the combined trial/saw guide of this invention may be constructed with prior knowledge of the final implant configuration, misalignments of the type discussed earlier with regard to the implant stem are minimized. Due to the fact that a single guide may be used to perform numerous, accurate cuts, the invention should save considerable time while increasing the precision of both primary and revision arthroplasty in a wide variety of joint replacement and other orthopaedic situations including the tibial side of a knee replacement.

Figure 6:
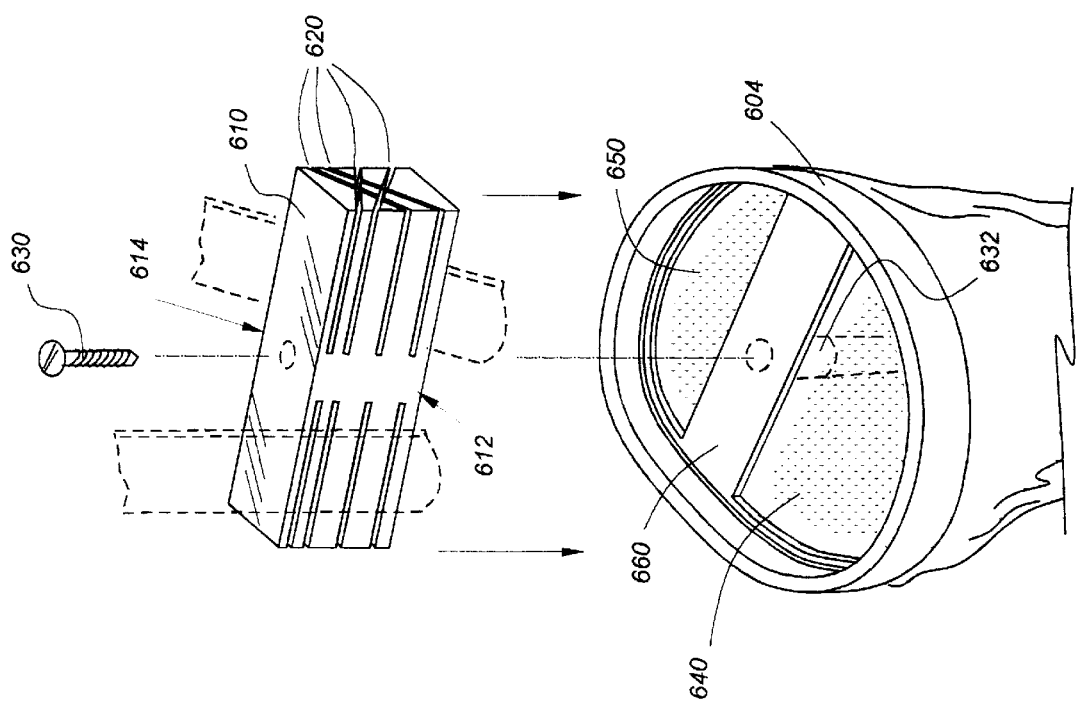
FIG. 6 represents yet a further alternative embodiment of the invention wherein cutting guides are provided on a central block.

FIG. 6 illustrates yet a further alternative embodiment of the invention wherein a base unit 604 is adapted to receive a cutting block 610 having surfaces such as 612 and 614 (not visible), as well as one or more slots 620. The block 610 may be fastened to the base unit 604 by a screw 630, or other suitable means, and, if a stem 632 is used, the same screw or fastener may be used to attach the block to the body to the stem. Openings 640 and 650 are provided on either side of the central piece 660, once again, to enable the saw or other cutting tool to pass therethrough and perform any necessary resections.

Figure 8:
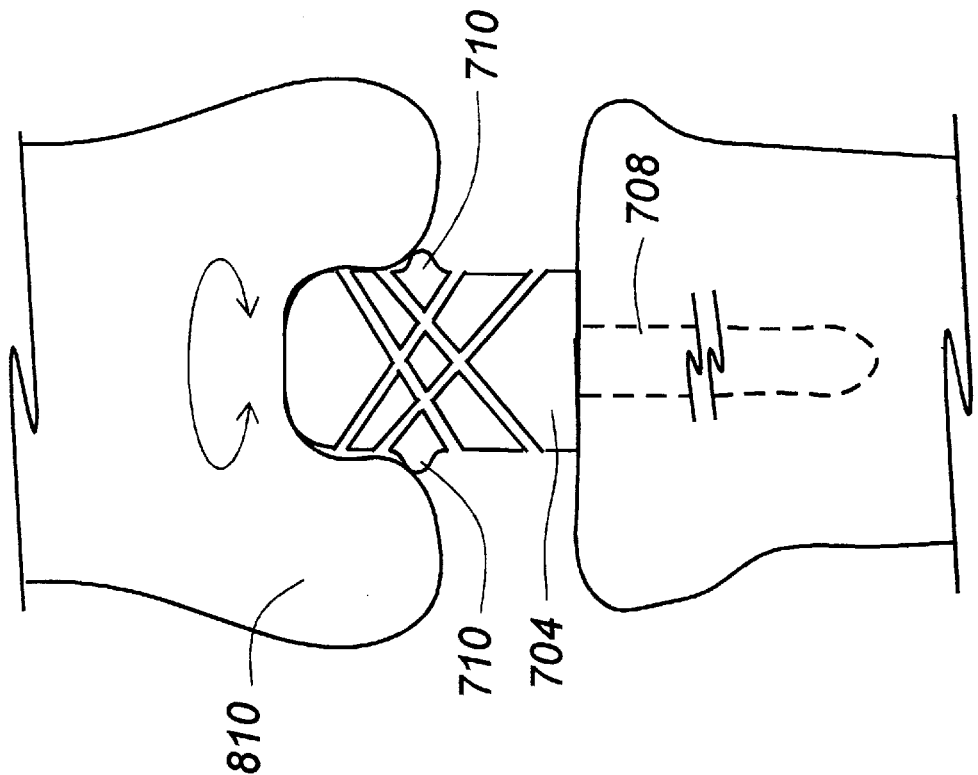
FIG. 8 illustrates how, with the addition of lengthwise ridges to the apparatus shown in FIG. 7, a partial trial reduction may be performed to ensure a correct rotation prior to resection of the tibia.
Figure 7:
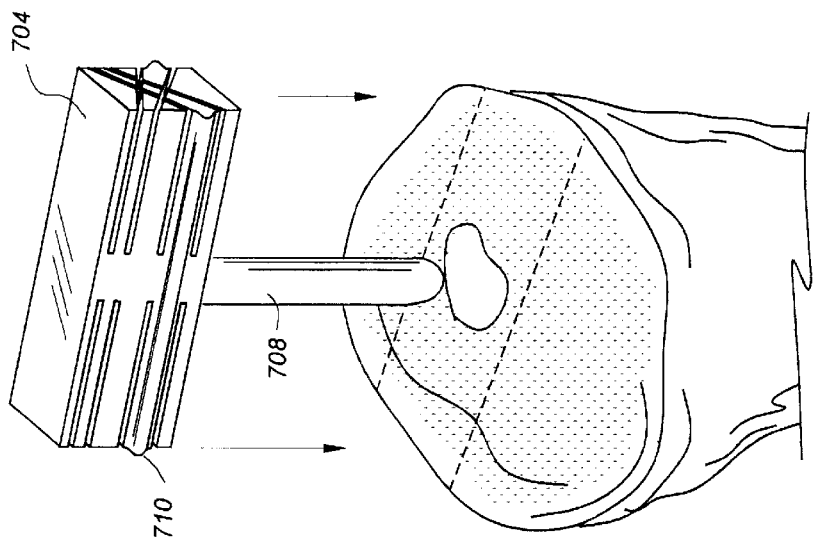
FIG. 7 illustrates another embodiment of the invention wherein a central cutting block attaches directly to a stem.

FIG. 7 illustrates two additional features according to the invention. Firstly, as an alternative to providing a base unit, a cutting block 704 may be attached directly to a stem 708. In addition, optional elongated ridges 710 may be provided, the function of which will be better understood with reference to FIG. 8. With the stem 708 in place, and with the block 704 attached thereto, if the ridges 710 are appropriately sized and shaped, a partial trial reduction may be performed, ether with a natural bone such as distal femur 810 or other bone or prosthetic element, enabling a rotation of the member 810 to be performed in conjunction with the block 704. Having assumed a proper rotation in this manner, the joint may be flexed and the block 704 used to make any necessary resections to remove deficiencies, as the case may be.

Having thus described my invention, I claim:

1. A bone-cutting guide adapted for use with a bone-cutting tool, comprising:
    a body having an outer surface and an inner surface, the inner surface being configured for placement against a bone surface to be modified, the outer surface of the body being adapted to receive an insert having an outer surface, and wherein the outer surface of the insert is shaped so as to co-act in a joint as part of a trial reduction;
    at least one aperture extending through the body from the outer surface to the inner surface; and
    one or more separate and removable guide blocks, each block having a first surface adapted for positioning relative to the outer surface of the body, and a second surface for stabilizing the movement of the bone-cutting tool at a desired angle through the aperture.

2. The bone-cutting guide of claim 1, including a guide block which is wedge-shaped, such that the desired angle is non-perpendicular with respect to the bone surface to be modified.

3. The bone-cutting guide of claim 1, including a guide block having first and second surfaces configured such that the desired angle is a right angle with respect to the bone surface to be modified.

4. The bone-cutting guide of claim 1, wherein the inner surface is flat.

5. The bone-cutting guide of claim 1, wherein the outer surface is flat.

6. The bone-cutting guide of claim 1, wherein the outer surface is shaped so as to co-act in a joint as part of a trial reduction.

7. The bone-cutting guide of claim 6, wherein the outer surface is shaped according to a natural proximal tibia, enabling the cutting guide to co-act in a knee joint as part of a trial reduction.

8. The bone-cutting guide of claim 1, wherein the outer surface is shaped according to a natural proximal tibia, enabling the cutting guide to co-act in a knee joint as part of a trial reduction.

9. The bone-cutting guide of claim 1, wherein the insert includes one or more apertures aligned with those of the body, enabling a bone-cutting tool to extend therethrough.

10. A bone-cutting guide adapted for use with a bone-cutting tool, comprising:
    a body having an outer surface and an inner surface, the inner surface being configured for placement against a bone surface to be modified;
    an insert having an inner surface configured for placement relative to the outer surface of the body and an outer surface shaped so as to co-act in a joint as part of a trial reduction;
    at least one aperture extending through the insert and the body; and
    one or more cutting blocks, each block having a first surface adapted for positioning relative to the outer surface of the insert, and a second surface for stabilizing the movement of the bone-cutting tool at a desired angle through the insert and body.

11. The bone-cutting guide of claim 10, including a guide block which is wedge-shaped, such that the desired angle is non-perpendicular with respect to the bone surface to be modified.

12. The bone-cutting guide of claim 10, including a guide block having first and second surfaces configured such that the desired angle is a right angle with respect to the bone surface to be modified.

13. The bone-cutting guide of claim 10, wherein the outer surface of the insert is shaped according to a natural proximal tibia, enabling the cutting guide to co-act in a knee joint as part of a trial reduction.

* * * * *